United States Patent [19]

Klingler et al.

[11] 4,317,832

[45] Mar. 2, 1982

[54] INDOLYL AND METHYLINDOLYL SUBSTITUTED AMINOALKYL GUANIDINES

[76] Inventors: Karl-Heinz Klingler, Lortzingstrasse 9, 607 Langen; Axel Kleemann, Greifenhagenstrasse 9, 6450 Hanau 9; Fritz Stroman, Herm. Steinh. Str. 18, 6050 Offenbach; Klaus Thiemer, Fürstenbergstrasse 12, 6450 Hanau 9, all of Fed. Rep. of Germany

[21] Appl. No.: 72,777

[22] Filed: Sep. 5, 1979

[30] Foreign Application Priority Data

Sep. 6, 1978 [GB] United Kingdom ............... 35819/78

[51] Int. Cl.³ .................... A61K 31/40; C07D 209/14
[52] U.S. Cl. ............................ 424/274; 260/326.15; 260/315; 424/238; 424/273 P; 424/270; 424/326; 546/145; 546/176; 548/154
[58] Field of Search .................... 260/326.15; 424/274

[56] References Cited

U.S. PATENT DOCUMENTS

| | | | |
|---|---|---|---|
| 3,317,570 | 5/1967 | Claassen | 260/326.15 |
| 3,471,515 | 10/1969 | Troxler et al. | 260/326.15 |
| 3,499,003 | 3/1970 | Welstead | 260/326.15 X |
| 3,501,497 | 3/1970 | Bell | 260/326.15 |
| 3,542,873 | 11/1970 | Faith | 564/351 |
| 3,644,353 | 2/1972 | Lunts et al. | 260/326.5 X |
| 3,821,301 | 6/1974 | Klingler | 564/237 |
| 4,144,340 | 3/1979 | Ottermans | 424/253 |

FOREIGN PATENT DOCUMENTS

| | | |
|---|---|---|
| 778027 | 1/1972 | France . |
| 7917180 | 7/1979 | France . |
| 1398918 | 6/1975 | United Kingdom . |

*Primary Examiner*—Donald G. Daus
*Assistant Examiner*—D. B. Springer
*Attorney, Agent, or Firm*—Cushman, Darby & Cushman

[57] ABSTRACT

Compounds corresponding to the formula

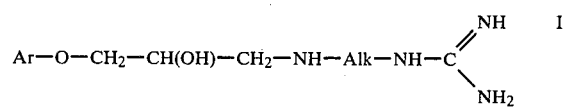

are disclosed, wherein Alk represents a $C_2$-$C_5$-alkylene groups optionally substituted by a hydroxy group and Ar represent an optionally substituted phenyl, naphthyl, tetrahydronaphthyl, indanyl or indenyl radical or a monocyclic or condensed bicyclic or tricyclic heterocyclic radical which is optionally substituted, the heterocyclic radical consisting of individual rings having 5 or 6 members and optionally containing from 1 to 4 hetero atoms, and the acid addition salts thereof. A process for producing these compounds is also disclosed. These substituted aminoalkyl guanidines block the β-receptors of the adrenergic nerve system, and also reduce blood pressure.

14 Claims, No Drawings

INDOLYL AND METHYLINDOLYL SUBSTITUTED AMINOALKYL GUANIDINES

BACKGROUND OF THE INVENTION

The present invention relates to substituted aminoalkyl guanidines, and a method for their preparation.

British Pat. No. 1,398,918 and related Klingler U.S. Pat. No. 3,821,301 describe compounds corresponding to the following general formula:

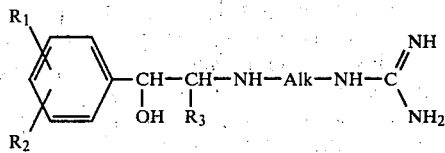

wherein $R_1$ represents hydrogen or a hydroxy group, $R_2$ represents a hydroxy group, a hydroxymethyl group or a $C_1$-$C_6$-alkyl group, $R_3$ represents hydrogen or a $C_1$-$C_4$-alkyl group and Alk represents a linear or branched $C_2$-$C_6$-alkylene group.

These compounds have a broncholytic effect and also show coronary-dilating and positive inotropic activity.

SUMMARY OF THE INVENTION

The present invention relates to substituted aminoalkyl guanidines corresponding to the following general formula:

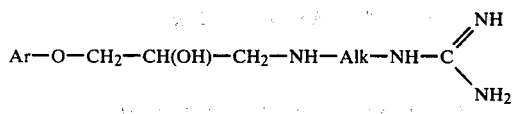

wherein Alk represents a $C_2$-$C_5$-alkylene group optionally substituted by a hydroxy group and Ar represents an unsubstituted phenyl, naphthyl, tetrahydronaphthyl, indanyl or indenyl radical or a phenyl, naphthyl, tetrahydronaphthyl, indanyl or indenyl radical substituted one or more times by a $C_1$-$C_6$-alkyl group, a $C_2$-$C_6$-alkenyl group, a $C_2$-$C_6$-alkinyl group, a hydroxy group, an aliphatic $C_1$-$C_6$-acyloxy group, a $C_1$-$C_6$-alkoxy group, a $C_2$-$C_6$-alkenoxy group, a phenyl radical, a halogen atom, an amino group, an aliphatic $C_2$-$C_6$-acyl group, an aminocarbonyl group, an ureido group, an aliphatic $C_1$-$C_6$-acylamino group, a $C_3$-$C_8$-cycloalkyl group or by a $C_4$-$C_8$-cycloalkenyl group, or a monocyclic or condensed bicyclic or tricyclic heterocyclic radical optionally substituted in the same way as defined above, the heterocyclic radical consisting of one or more individual rings each having 5 or 6 members and optionally containing from 1 to 4 hetero atoms, and the acid addition salts thereof especially the acid addition salts with pharmaceutically acceptable acids.

The compounds according to the present invention are pharmacodynamically active. Their main effect is that they block the $\beta$-receptors of the adrenergic nerve system (the effects of isoprenaline on the circulation are inhibited). In addition, they reduce blood pressure.

The compounds according to the present invention have a wide therapeutic scope and are distinguished by minimal side effects. They may be present in a medicament which comprises at least one substituted aminoalkyl guanidine together with at least one pharmacologically acceptable inert excipient and/or carrier; said medicament being prepared by simply mixing the components.

The present invention also relates to a process for the production of a compound corresponding to general formula I which comprises (a) reacting an amine corresponding to the following general formula:

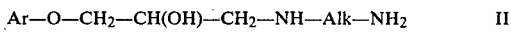

$$Ar-O-CH_2-CH(OH)-CH_2-NH-Alk-NH_2 \qquad II$$

wherein Ar and Alk are as defined above, with a compound corresponding to the following general formula:

wherein E represents an amino group which may also contain a protective acyl group, e.g., an acyl group of a carboxylic acid, or represent a $C_1$-$C_6$-alkyl mercapto group of $C_1$-$C_6$-alkoxy group or, together with $NH_2$, may also form the group $=NH$. or (b) reacting a compound corresponding to the following general formula:

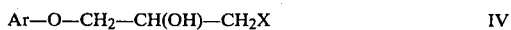

$$Ar-O-CH_2-CH(OH)-CH_2X \qquad IV$$

wherein Ar is as defined above and X represents a hydroxy group which is esterified by a strong organic or inorganic acid and which, in non-esterified form, may form the ethylene oxide ring together with the adjacent, second hydroxy group, with an aminoalkyl guanidine corresponding to the following general formula:

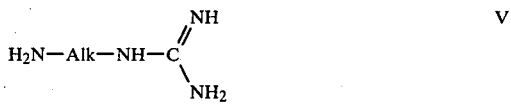

wherein Alk is as defined.

In the compounds according to the invention as represented by formula I, the alkylene group Alk preferably consists of 2, 3, or 4 carbon atoms (ethylene group, propylene groups, butylene groups, —$CH_2$—$CH(OH)$—$CH_2$, —$CH_2$—$CH(OH)$—$(CH_2)_2$—, or —$(CH_2)_2$—$CH(OH)$—$CH_2$ groups).

If the group Alk is branched, it contains in particular 3, 4 or 5 carbon atoms (for example, —$CH_2$—$CH_2$—$CH(CH_3)$—, —$CH_2$—$CH(CH_3)$—, —$CH_2$—$CH(CH_3)$—$CH_2$—, —$CH_2$—$CH(CH_3)$—$CH(CH_3)$—, or —$CH_2$—$CH(OH)$—$CH(CH_3)$—). Any hydroxy group present is always in the alkylene moiety of Alk, particularly in the $\beta$-position to the guanidino group. (If Alk is, for example, the trimethylene group

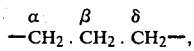

the $\alpha$-position is the position adjacent the guanidino group.)

The radical Ar represents, for example, the phenyl or the 1-naphthyl radical. If Ar represents a heterocyclic radical, the heterocyclic radical in question is, for example, a monocyclic 5-membered or 6-membered aromatic ring containing one nitrogen, sulphur or oxygen atom or two nitrogen atoms, or an aromatic condensed bicyclic radical of a phenyl ring having a 5-membered or 6-membered ring attached by condensation, in which case the ring attached by condensation may contain a nitrogen, oxygen or sulphur atom. In the bicyclic rings, the radical Ar is attached to the oxygen atom in particular through the 4- or 5-position of the phenyl ring. The following are examples of the heterocyclic radical Ar which may also be unsubstituted or substituted as defined above: indole, isoindole, benzimidazole, quinoline, dihydroquinoline, tetrahydroquinoline, isoquinoline, pyrazole, thiazole, methyl indole, e.g., 2-methyl indole, methyl isoindole, methyl benzimidazole, methyl quinoline, methyl dihydroquinoline, methyl tetrahydroquinoline, methyl isoquinoline, methyl pyrazole, methyl thiazole, dimethyl indole, dimethyl quinoline, dimethyl isoquinoline, carbazole, or dimethyl benzimidazole. In the bicyclic radicals, the methyl group or groups is/are preferably situated in the ring containing the hetero atom.

The radical Ar may be substituted particularly by the following groups: $C_1$–$C_4$-alkyl, for example methyl, ethyl, propyl, isopropyl, tert.-butyl, or butyl; $C_2$–$C_5$-alkenyl, preferably vinyl, allyl, methallyl, or crotyl; $C_2$–$C_5$-alkinyl, for example, propargyl; cycloalkyl having a ring size of from 5 to 8 carbon atoms, preferably cyclopentyl, cyclohexyl, or cycloheptyl; cycloalkenyl having a ring size of from 5 to 8 carbon atoms, preferably cyclopentenyl, cyclohexenyl, or cycloheptenyl; $C_1$–$C_6$-alkoxy, for example methoxy, ethoxy, propoxy, isopropyloxy, butoxy, or tert.-butoxy; $C_2$–$C_5$-alkenyloxy and alkinyloxy, for example allyloxy, methallyloxy, or propargyloxy; halogen, preferably fluorine, bromine or chlorine; $C_2$–$C_6$-acyl, for example acetyl, propionyl, butyryl, pentanoyl, or isobutyryl; $C_1$–$C_5$-acylamino, for example acetamino, formylamino, propionylamino, butyrylamino, isobutyrylamino, or pentanoylamino; $C_2$–$C_6$, preferably $C_2$–$C_4$-hydroxy or acyloxy, such as acetoxy, propionyloxy, or butyryloxy; hydroxy; aminocarbonyl ($NH_2$—CO—) or ureido ($H_2N$—CO—NH—).

The substituents of Ar may be the same or different. The radical Ar may contain several of the above-mentioned substituents, preferably 1, 2 or even 3 of these substituents. Where Ar is a bicyclic heterocyclic ring, the ring in question preferably contains one of the above-mentioned substituents in the o-position to the hetero atom and/or an alkyl group on the nitrogen atom present, if any. The phenyl radical is substituted in particular (i.e., preferably) in theortho and/or para position.

In the context of the invention, the compounds corresponding to general formula I are also understood to include the possible stereoisomeric and optically active compounds and mixtures thereof, particularly the racemates. Mixtures of diastereoisomers can be separated by a known method, for example, by fractional crystallization. Optically active compounds may be obtained using the conventional methods, for example by recrystallizing salts of the racemic bases of formula I with optically active acids or, optionally, by using optically active starting materials at the synthesis stage.

The end products corresponding to formula I are obtained either in free form or in the form of their salts, depending on the process conditions applied and the starting materials used. The salts of the end products may be converted back into the bases by a known method, for example using alkali, e.g., sodium hydroxide, or using ion exchangers. Salts may be obtained from these bases by reaction with organic or inorganic acids, particularly those which are suitable for forming therapeutically usable salts. Acids such as these are, for example, hydrohalic acids, e.g., hydrochloric acid and hydrobromic acid, sulphuric acid, acids of phosphorus, e.g., phosphoric acid and phosphorous acid, nitric acid, perchloric acid, organic mono-, di- or tri-carboxylic acids of the aliphatic, alicyclic, aromatic or heterocyclic series and sulphonic acids. Examples of these acids are formic acid, acetic acid, propionic acid, succinic acid, glycolic acid, lactic acid, malic acid, tartaric acid, citric acid, ascorbic acid, maleic acid, fumaric acid, hydroxy maleic acid, pyruvic acid, phenyl acetic acid, benzoic acid, p-aminobenzoic acid, anthranilic acid, p-hydroxy benzoic acid, salicylic acid, p-aminosalicylic acid, embonic acid, methane sulphonic acid, ethane sulphonic acid, hydroxy ethane sulphonic acid, ethylene sulphonic acid; halogen benzene sulphonic acid, e.g., p-chlorobenzene sulphonic acid, toluene sulphonic acid, naphthalene sulphonic acid or sulphanilic acid or even 8-chlorotheophylline.

In addition to the compounds mentioned in the working examples, other compounds within the invention include 2-[3-phenoxy-2-hydroxypropylamino]-ethyl guanidine,
5-[3-phenoxy-2-hydroxypropylamino]-amyl guanidine,
3-{3-[naphthyl-(1)-oxy]-2-hydroxylpropylamino}-2-hydroxypropyl guanidine as well as the compounds of the formula

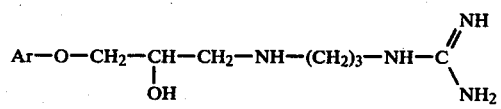

where Ar is
   isoindolyl-(4)-
   benzimidazolyl-(4)-
   quinolyl-(2)-
   quinolyl-(5)-
   dihydroquinolyl-(5)-
   tetrahydroquinolyl-(5)-
   isoquinolyl-(2)-
   isoquinolyl-(5)-
   pyrazolyl-(3)-
   thiazolyl-(2)-
   thiazolyl-(5)-
   3-methylisoindolyl-(4)-
   1,2-dimethyl indolyl-(4)-
   2,3-dimethyl indolyl-(4)-
   2,3-dimethyl quinolyl-(5)-
   phenyl
   p-methylphenyl-
   2,4-dimethylphenyl-
   2-methyl-4-chlorophenyl-
   2-bromophenyl
   2,4-dichlorophenyl-
   2,4,5-trichlorophenyl-
   4-n-butylphenyl-
   4-t-butylphenyl-
   2-ethylphenyl-
   4-isopropylphenyl-
   2-vinylphenyl-
   4-allylphenyl- 4-methallylphenyl-
2-crotylphenyl
4-propargylphenyl-
2-cyclohexylphenyl-
4-cyclohexylphenyl-
2-cyclopentylphenyl-
4-cycloheptylphenyl-
4-cyclooctylphenyl-
4-methoxyphenyl-
2,4-dimethoxyphenyl-
2,4,5-trimethoxyphenyl-
4-ethoxyphenyl-
2-isopropoxyphenyl-
4-propoxyphenyl-
4-butoxyphenyl-
2-t-butoxyphenyl-
4-hexoxyphenyl-
2-cyclopentenylphenyl-
4-cyclohexenylphenyl-
4-cycloheptenylphenyl-
4-methallyloxyphenyl-
2-propargyloxyphenyl-
2-acetylphenyl-
4-acetylphenyl-
2-propionylphenyl-
4-butyrylphenyl-
2-pentanoylphenyl-
4-isobutyrylphenyl-
2-hexanoylphenyl-
2-acetaminophenyl-
4-formylaminophenyl-
2-propionylaminophenyl-
4-butyrylaminophenyl-
2-isobutyrylaminophenyl-
4-pentanoylaminophenyl-
2-hexanoylaminophenyl-
2-acetoxyphenyl-
4-acetoxyphenyl-
2-propionyloxyphenyl-
4-butyryloxyphenyl-
4-hexanoyloxyphenyl-
2-aminocarbonylphenyl-
4-aminocarbonylphenyl-
2-ureidophenyl-
4-ureidophenyl-
indanyl-(2)-
indanyl-(5)-
indenyl-(2)-
5,6,7,8-tetrahydronaphthyl-(2)-
2-hydroxyphenyl-
4-hydroxyphenyl-
2,4,-dihydroxyphenyl.

In the process described hereinafter for producing the compounds according to the invention, the amino groups entering into the reaction may contain conventional protective groups. These protective groups are radicals which may readily be eliminated by hydrolysis or hydrogenolysis and which, in many cases, are even eliminated during the actual reaction. If these protective groups are not eliminated during the reaction on which the process is based, they are eliminated after the reaction. In many cases, the starting compounds themselves contain protective groups of this type due to the method of their own production.

Protective groups of this type are, for example, acyl groups which can readily be eliminated by solvolysis or groups which can be eliminated by hydrogenation. The protective groups removable by solvolysis are eliminated for example by hydrolysis using dilute acids, e.g., hydrochloric acid or sulphuric acid, or by means of basic substances (potash, soda, aqueous alkali solutions, e.g., aqueous sodium hydroxide, alcoholic alkali solutions, e.g., sodium hydroxide in ethanol or $NH_3$) at a temperature in the range of from 10° to 150° C. and, more particularly, at a temperature in the range of from 20° to 100° C. Groups removable by hydrogenation, such as α-aryl alkyl radicals (benzyl radical) or hydroxy carbonyl radicals (carbobenzoxy radical), are best eliminated by catalytic hydrogenation in the presence of conventional hydrogenation catalysts, particularly palladium catalysts, platinum oxide or even Raney nickel, in a solvent or suspending agent, optionally under elevated pressure, at a temperature in the range of from 20° to 100° C. and more particularly at a temperature in the range of from 40° to 80° C. Examples of suitable solvents or suspending agents are water, lower aliphatic alcohols, e.g., methanol, ethanol and isopropanol, cyclic ethers, such as dioxane or tetrahydrofuran, aliphatic ethers, e.g., diethyl ether, or dimethyl formamide and also mixtures thereof.

Examples of protective groups which can be eliminated by hydrogenolysis are the benzyl radical, the α-phenylethyl radical, benzyl radicals substituted in the benzene nucleus (the p-bromo or p-nitrobenzyl radical), the carbobenzoxy radical, the carbobenzthiazole radical, or the tert.-butyl hydroxy carbonyl radical. Examples of radicals which can be eliminated by hydrolysis are the trifluoroacetyl radical, the phthalyl radical, the trityl radical, or the p-toluene sulphonyl radical, and also lower alkanoyl radicals, such as the acetyl radical, the formyl radical, or the tert.-butyl carboxy radical.

The protective groups commonly encountered in the synthesis of peptides and the methods by which they are normally eliminated are particularly suitable. In this connection, reference is made inter alia to the book by Jesse P. Greenstein and Milton Winitz entitled "Chemistry of Amino Acids", John Wiley and Sons, Inc., N.Y., 1961, Volume 2, for example pages 883 et seq. The carbalkoxy group (for example of low molecular weight) is also suitable.

If the starting materials additionally contain alcoholic hydroxy groups and/or primary amino groups, these groups may also be protected by the above-mentioned protective groups which may be eliminated in the same way.

The production of substituted aminoalkyl guanidines according to method (a)

The reaction may be carried out in solution or in the melt at a temperature in the range of from 20° to 150° C., optionally under elevated pressure. Suitable solvents are, for example, water or organic solvents, such as alcohols, e.g., those mentioned above, toluene, xylene, dioxane, or alcohol-water mixtures. The compounds corresponding to the following general formula:

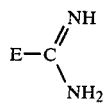

III wherein E is an amino group which may also contain a protective acyl group or represents a $C_1-C_{16}$-alkyl mercapto group or $C_1-C_6$-alkoxy group or, together with $NH_2$, may also form the group =NH, may be used in the form of the free base or even in the form of the usual acid addition salts (for example sulphates or hydrochlorides). If, in formula III, E and the group —NH₂ together form the group =NH, the compound in question is the carbonic acid diimide or cyanamide.

The starting materials corresponding to the following general formula:

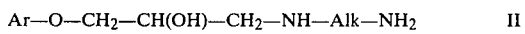

wherein Ar and Alk are as defined above, may be obtained by using a known method. One such method is to react compounds corresponding to the formula Ar—O—CH₂—CH(OH)—CH₂—Hal (wherein Hal represents chlorine, bromine or iodine) or halogen hydrins corresponding to the formula:

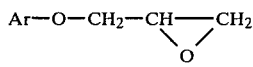

with a diamine of the formula H₂N—Alk—NH₂. The diamine is preferably used in excess. In cases where asymmetrical branched diamines are used, it is best to protect the amino group which is not intended to react with the other reaction component before the reaction. The benzyl group for example has proved to be particularly suitable for this purpose because, on completion of the reaction, it may be removed in known manner under mild conditions.

The production of substituted aminoalkyl guanidines according to method (b)

The reaction on which this method is based may be carried out in the absence of additional solvent or in the presence of a suitable solvent or dispersant. Suitable solvents or dispersants are, for example, aromatic hydrocarbons such as benzene, mesitylene, toluene or xylene; ketones such as acetone or methylethyl ketone; halogenated hydrocarbons such as chloroform, carbon tetrachloride, chlorobenzene, or methylene chloride; ethers such as tetrahydrofuran or dioxane; sulphoxides such as dimethyl sulphoxide; tertiary acid amides such as dimethyl formamide or N-methyl pyrrolidone; and alcohols such as methanol, ethanol, isopropanol, amyl alcohol, or tert.-butanol. The reaction is carried out for example at a temperature in the range of from 20° C. to 200° C., preferably at a temperature in the range of from 50° C. to 180° C. or even at a temperature in the range of from 80° C. to 120° C. If a solvent or dispersant is used, the reaction is frequently carried out at the reflux temperature thereof. In many cases, the reaction even takes place at normal temperature or at a temperature in the range of from 20° to 50° C.

It may be advisable to use the starting compounds corresponding to the following general formula:

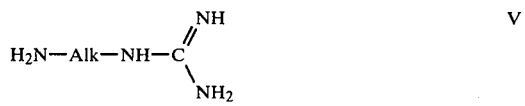

wherein Alk is as defined above, in excess and/or to add the reaction component corresponding to the following general formula:

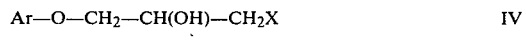

wherein Ar is as defined above and X represents a hydroxy group which is esterified by a strong organic or inorganic acid and which, in non-esterified form, may form the ethylene oxide ring together with the adjacent, second hydroxy group, in dissolved or suspended form to the dissolved or suspended reaction component of general formula V. The molar ratio between the compounds corresponding to general formula IV and V generally amounts to from 1:1 to 1:10 and, in some cases, may even be higher.

For carrying out the reaction, the ethylene oxide compound may even be replaced as the ethylene oxide starting compound by the corresponding halogen hydrin or by a mixture of these two compounds (crude synthesis product).

The reaction may even be carried out in the presence of acid-binding agents, such as alkali carbonates, potash, soda, alkali hydroxides or tertiary bases, e.g., triethyl amine.

If X represents an esterified hydroxy group, the compounds in question are reactive esters. A reactive ester is, for example, the ester of a strong organic or inorganic acid, such as, in particular, a hydrohalic acid, for example hydrochloric acid, hydrobromic acid or hydriodic acid, or a sulphonic acid, such as an aryl or alkyl sulphonic acid, for example, p-toluene sulphonic acid. Where a reactive ester is used, the reaction is advantageously carried out in the presence of a basic condensation agent or an excess of amine. Suitable solvents are, in particular, dioxane/water, dimethyl formamide/water or lower saturated aliphatic alcohols such as any of those mentioned previously.

Starting compounds corresponding to formula IV and/or V may also contain protective groups, for example a benzyl group. If, as mentioned above, protective groups of the type in question are not eliminated during the actual reaction, they may be removed on completion of the reaction by the methods already described.

The compounds according to the invention are suitable for the production of pharmaceutical compositions and preparations. The pharmaceutical compositions or medicaments contain, as active principle, one or more of the compounds according to the invention, optionally in admixture with other pharmacologically or pharmaceutically active substances. The medicaments may be prepared with the usual pharmaceutical excipients, assistants, carriers, and diluents.

As carriers and assistants, for example, are those recommended in the following literature as adjuvants for pharmacy, cosmetic and related fields such as in Ullmann's Encyklopädie der technischen Chemie, Volume 4 (1953), pages 1 to 39; Journal of Pharmaceutical Sciences 52 (1963), pages 918 et seq., H. V. Czetsch-Lindenwald, Hilfstoffe fur Pharmazie and angrenzende Gebiete; Phar. Ind. 2 (1961), pages 72 et seq., Dr. H. P. Fiedler, Lexicon der Hilfstoffe fur Pharmazie, Kosmetik und angrenzende Gebiete, Cantor Kg. Aulendorf i. Württ. (1971).

Examples of such materials include gelatin, natural sugars such as sucrose or lactose, lecithin, pectin, starch (for example cornstarch), alginic acid, tylose, talc, lycopodium, silica (for example colloidal silica), glucose, cellulose, cellulose derivatives for example cellulose ethers in which the cellulose hydroxyl groups are partially etherified with lower aliphatic alcohols and/or lower saturated oxyalcohols (for example methyl hydroxypropyl cellulose, methyl cellulose, hydroxyethyl cellulose), stearates, e.g., methylstearate and glyceryl stearate, magnesium and calcium salts of fatty acids with 12 to 22 carbon atoms, especially saturated acids (for example calcium stearate, calcium laurate, magnesium oleate, calcium palmitate, calcium behenate and magnesium stearate), emulsifiers, oils and fats, especially of plant origin (for example peanut oil, castor oil, olive oil, sesame oil, cottonseed oil, corn oil, wheat germ oil, sunflower seed oil, cod-liver oil), mono-, di- and triglycerides of saturated fatty acids ($C_{12}H_{24}O_2$ to $C_{18}H_{36}O_2$ and their mixtures, e.g., glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400 and other polyethylene glycols, as well as derivatives of such alcohols and polyglycols, esters of saturated and unsaturated fatty acids (2 to 22 carbon atoms, especially 10 to 18 carbon atoms), with monohydric aliphatic alcohols (1 to 20 carbon atoms alkanols) or polyhydric alcohols such as glycols, glycerine, diethylene glycol, pentaerythritol, sorbitol, mannitol, ethyl alcohol, butyl alcohol, octadecyl alcohol, etc., e.g., glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case also be etherified benzyl benzoate, dioxolane, glycerine formal, tetrahydrofurfuryl alcohol, polyglycol ethers with 1 to 12 carbon atom alcohols, dimethyl acetamide, lactamide, lactates, e.g., ethyl lactate, ethyl carbonate, silicones (especially middle viscosity dimethyl polysiloxane), magnesium carbonate and the like.

For the production of solutions there can be used water or physiologically compatible organic solvents as for example, ethanol, 1,2-propylene glycol, polyglycols, e.g., diethylene glycol, triethylene glycol and dipropylene glycol and their derivatives, dimethyl sulfoxide fatty alcohols, e.g., stearyl alcohol, cetyl alcohol, lauryl alcohol and oleyl alcohol, triglycerides, e.g., glyceryl oleate, glyceryl stearate, glyceryl palmitate, and glyceryl acetate, partial esters of glycerine, e.g., monoacetic, diacetin, glyceryl monostearate, glyceryl distearate, glyceryl monopalmitate, paraffins and the like.

In the production of the preparation there can be used known and customary solution aids or emulsifiers. As solution aids and emulsifiers there can be used, for example, polyvinyl pyrrolidone, sorbitan fatty acids esters such as sorbitan trioleate, lecithin, gum acacia, gum tragacanth, polyoxyethylated sorbitan monoleate, polyoxyethylated fats, polyoxyethylated oleotriglycerides, linolized oleotriglycerides, polyethylene oxide-condensation products of fatty alcohols, alkylphenols or fatty acids. As used herein polyoxyethylated means that the materials in question contain polyoxyethylene chains whose degree of polymerization generally is between 2 and 40, particularly between 10 and 20.

Such polyoxyethylated materials for example can be obtained by reaction of hydroxyl group containing compounds (for example mono- or diglycerides) or unsaturated compounds such as, for example, those containing the oleic acid radical with ethylene oxide (for example 40 moles of ethylene oxide per mole of glyceride).

Examples of oleotriglycerides are olive oil, peanut oil, castor oil, sesame oil, cottonseed oil, corn oil (see also Dr. H.P. Fiedler, supra, pages 191-195).

Furthermore, there can be added preservatives, stabilizers, buffers, for example, calcium hydrogen phosphate, colloidal aluminum hydroxide, taste correctives, antioxidants and complex formers (for example ethylene diamine tetracetic acid) and the like. In a given case for stabilization of the active molecule the pH is adjusted to about 3 to 7 with physiologically compatible acids or buffers. Generally, there is preferred as neutral as possible to weak acid (to pH 5) pH value. As antioxidants there can be used for example sodium metabisulfite, ascorbic acid, gallic acid, alkyl gallates, e.g., methyl gallate and ethyle gallate, butyl hydroxyanisole, nordihydroguararetic acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatives there can be used for example sorbic acid, p-hydroxybenzoic acid esters (for example lower alkyl esters such as the methyl ester and the ethyl ester), benzoic acid, sodium benzoate, trichloroisobutyl alcohol, phenol, cresol, benzethonium chloride and formalin, derivatives).

The pharmacological and galenical treatment of the compounds of the invention takes place according to the usual standard method. For example, the active material or materials and assistants or carriers are well mixed by stirring or homogenization (for example by means of a colloid mill or ball mill), wherein the operation is generally carried out at temperatures between 20° and 80° C., preferably 20° to 50° C.

The application of active material or drug can take place on the skin or mucous membrane or internally, for example, orally, enterally, pulmonally, rectally, intravenously, nasally, vaginally, lingually, intravenously, intraarterially, intracardially, intramuscularly, intraperitoneally, subcutaneously or intracutaneously.

The addition of other medicines is also possible or favorable.

On awake rabbits (method according to Bartsch et al, Arzneimittelforschung (Drug Res.), Volume 24, 303 (1974)), the compounds of the invention exhibit a good $\beta$-adrenolytic activity with a tachycardia caused by isoprenaline. Thus, for example, there is found in rabbits with intravenous application an $ED_{50}$ of 0.007 mg/kg. The arterial pressure in narcotized dog is clearly reduced whereby simultaneously the heart time volumes are reduced because of the lowering of the heart frequency while the vascular resistance, for example, is only slightly changed or likewise is reduced. Ascertaining the blood pressure and the heart frequency, for example, takes place on the narcotized dog by means of an electronic manometer in combination with a direct recorder. The heart frequency is ascertained thereby from the recorded curve by counting the individual impulses per minute. The heart time volumes is determined with the help of the cold dilution method according to H. Slama and J. Piiper, Kreislaufforschung, Volume 53, page 322 (1964). The peripheral vascular resistance can then be calculated from the heart time volumes and average arterial blood pressure in known manner. For example, there was observed after injecting 1 mg/kg intravenously in the dog a lowering of the average arterial of around 35%, a reduction of the heart frequency of around 13% a reduction of the heart time volume of around 10% and a reduction of the total resistance of the peripheral blood vessels of around 27%. These activities are comparable with the action of the known medicine Acebutol.

The lowest clearly β-adrenolytically effective dosage in the above-stated animal tests, for example, is 0.03 mg/kg orally and 0.003 mg/kg intravenously.

The lowest clearly blood pressure lowering dosage in the above-stated animal tests, for example, is 0.3 mg/kg orally and 0.03 mg/kg intravenously.

As the general dosage range for the blood pressure lowering and β-adrenolytic effect (animal experiments as above), there can be used, for example:

0.3 to 30 mg/kg orally, especially 1–10 mg/kg; 0.03 to 3 mg/kg intravenously, especially 0.1–1 mg/kg.

The compounds of the invention are indicated for: essential and renal hypertonia, angina pectoris, chronic coronary insufficiency, disturbance in the formation of stimulation of the heart and in the extending of the stimulation of the heart.

The pharmaceutical preparations generally contain between 3 and 300 mg of the active component or components of the invention.

The compounds can be delivered in the form of tablets, capsules, pills, dragees or in liquid form. As liquid forms there can be used, for example, oily or alcoholic or aqueous solutions as well as suspensions and emulsions. The preferred forms of use are tablets which contain between 10 and 200 mg or solutions which contain between 0.5 and 5% of active material.

In individual doses, the amount of active components of the invention can be used for example in an amount of:

a. in oral dispensation between 10 and 400 mg;
b. in parenteral dispensation (for example, intravenously, intramuscularly) between 10 and 50 mg.

For example, there is recommended the use of 1 to 3 tablets containing 10 to 200 mg of active ingredient 3 times daily or for example, intravenouusly the injection 1 to 3 times daily of a 2 to 10 ml ampoule containing 10 to 50 mg of active substance. In oral dispensation the minimum daily dosage for example is 150 mg; the maximum daily dosage in oral administration should not be over 1 gram.

The dosages in each case are based on the free base.

Based on animals studies as set forth above it would appear that the dosage in humans would be the same per kilogram of body weight. Thus with the known drug Acebutol there is a similar correlation between the dosage fed to animals and to humans.

The acute toxicity of the compounds of the invention in the mouse (expressed by the $LD_{50}$ mg/kg method of Miller and Tainter, Proc. Soc. Exper. Biol. an Med. 57 (1944), pages 261 et seq.) in oral application is between 100 mg/kg and 500 mg/kg.

The drugs can be used in human medicine, in veterinary medicine as well as in agriculture alone or in admixture with other pharamacologically active materials. The compounds can be used to treat dogs, cats, horses and cattle.

In the treatment of dogs and cats, the individual oral dosages are generally between about 1 and 3 mg/kg of body weight; the parenteral dosage between and 0.1 and 0.5 mg/kg body weight.

In the treatment of horses and cattle the individual oral dosages are generally between 1 and 3 mg/kg body weight; the parenteral dosages between about 0.3 and 1.0 mg/kg body weight.

The methods can comprise, consist essentially of or consist of the steps set forth with materials shown. The compositions can comprise, consist essentially of or consist of the materials set forth.

Unless otherwise indicated all parts and percentages are by weight.

The present invention is illustrated by the following examples.

DESCRIPTION OF THE PREFERRED EMBODIMENTS

Example 1

3-{3-[Naphthyl-(1)-oxy]-2-hydroxypropylamino}-propyl guanidine

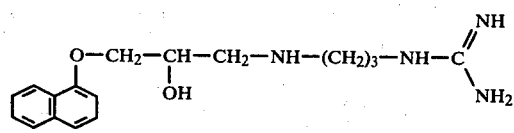

5.0 g of 3-{3-naphthyl-(1)-oxy]-2-hydroxypropylamino}-propylamine are dissolved in 50 ml of ethanol and 15 ml of water and the resulting solution is boiled under reflux with stirring for 10 hours together with 5.75 g of S-methyl isothiourea sulphate. A pH value of from 4 to 5 is maintained using 10% sulphuric acid, the sulphate precipitated is filtered off under suction and washed with water and acetone. The yield is 6.5 g, and the m.p. of the sulphate is 290°–293° C. (decomposition).

For conversion into the more soluble oxalate, the sulphate is stirred with sodium hydroxide and chloroform, and extracted by shaking three times with chloroform. The combined chloroform extracts are then dried over sodium sulphate, concentrated by evaporation and the alcoholic solution of the residue is acidified using an alcoholic oxalic acid solution (having a pH value of from 4 to 5). The oxalate which crystallizes out is filtered off under suction and recrystallized from water. The yield is 3.7 g, and the m.p. of the oxalate is 220° C. (decomposition).

Production of the starting product:

11.8 g of 3-[naphthyl-(1)-oxy]-2-hydroxypropyl chloride are added dropwise with stirring to 118 ml of 1,3-diaminopropane. After stirring for 1 hour at 60° C., the excess amine is distilled off in vacuo, and the residue is taken up in chloroform, and extracted by shaking three times with water. The chloroform phase is dried over potassium carbonate, concentrated by evaporation and the residual base is dissolved in ether. After acidification using alcoholic hydrochloric acid, the dihydrochloride obtained is filtered off under suction and recrystallized from isopropanol. (The yield is 8 g, and the m.p. is 180°–190° C).

To produce the base, the dihydrochloride is dissolved in water, alkalized with sodium hydroxide and extracted by shaking with butanol. The residue obtained after drying and concentration by evaporation is directly used for the next stage.

The compounds corresponding to the following general formula:

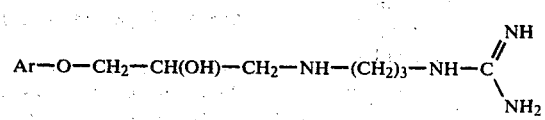

listed in Table 1a are obtained in the same way as described in Example 1 from the corresponding amine Ar—O—CH$_2$—CH(OH)—CH$_2$—NH—(CH$_2$)$_3$NH$_2$ and S-methyl isothiourea or O-methyl isourea.

The corresponding quantities of the starting components are shown in Table 1b. Some minor differences from Example 1 are mentioned in the fourth column of Table 1b.

The starting materials used, which are identified in column 2 of Table 1b, may be produced in the same way as the starting material used in Example 1.

TABLE 1a

| Example No. | Ar | Melting point as sulphate | Yield (g)/remarks |
|---|---|---|---|
| 2 | 2-methylphenyl (CH$_3$ ortho) | 272–274° C. | 11.3 |
| 3 | 3-methylphenyl (CH$_3$ meta) | 278–279° C. | 10.6 |
| 4 | 2-methoxyphenyl (OCH$_3$ ortho) | 256–258° C. | 4.3; recrystallized from H$_2$O |
| 5 | 2-allyloxyphenyl (CH$_2$=CH—CH$_2$—O, ortho) | 240–244° C. | 11.8; recrystallized from H$_2$O |
| 6 | 4-allyloxyphenyl (allyl-O, para) | 240–241° C. | 8.7 |
| 7 | 2-chlorophenyl (Cl ortho) | 268–270° C. | 13.4; dihydrochloride: from sulphate and BaCl$_2$ in boiling H$_2$O, m.p. 123–125° C. (from isopropanol) |
| 8 | 4-chlorophenyl (Cl para) | 281–283° C. (from H$_2$O) | 19 |
| 9 | 4-methylindol-yl | 233–235° C. (recrystallized (from H$_2$O)) | 2,1; di-8-chlorotheophyllinate: from 1 mole of base and 2 moles of 8-chlorotheophylline in boiling ethanol, m.p. 190–197° C. |
| 10 | 2-methylindol-yl | 230–234° C. | 2.6; recrystallized from 50% methanol |
| 11 | 4-methylcarbazol-yl | 231–235° C. | 8.1; recrystallized from 40% aqueous dimethyl acetamide. |

TABLE 1b

| Example No. | Starting material Ar—O—CH$_2$—CH(OH)—CH$_2$NH / H$_2$N—(CH$_2$)$_3$— | Yield of S-methyl isothiourea (as sulphate) | Different solvent from Example 1 |
|---|---|---|---|
| 2 | 10.8 g; Ar = 2-methylphenyl (CH$_3$) | 12.9 g | 100 ml of ethanol + 30 ml of H$_2$O |
| 3 | 10 g; Ar = 3-methylphenyl (CH$_3$) | 11.95 g | 10 ml of ethanol + 30 ml of H$_2$O |
| 4 | 7.6 g; Ar = 2-methoxyphenyl (OCH$_3$) | 3.7 g of O-methyl isourea sulphate | 25 ml of water |

TABLE 1b-continued

| Example No. | Starting material Ar—O—CH₂—CH(OH)—CH₂NH—(CH₂)₃—NH₂ | Yield of S-methyl isothiourea (as sulphate) | Different solvent from Example 1 |
|---|---|---|---|
| 5 | 16 g; Ar = (2-allyloxyphenyl, CH₂=CH—CH₂O-) | 19 g | 200 ml of ethanol + 60 ml of water |
| 6 | 16 g; Ar = allyl-O—C₆H₄— | 19 g | 200 ml of ethanol + 60 ml of water |
| 7 | 16.5 g; Ar = (2-chloro-6-methylphenyl) | 22.6 g | 200 ml of ethanol + 60 ml of water, boiling for 2 hours |
| 8 | 16.5 g; Ar = Cl—C₆H₄— | 22.6 g | 200 ml of ethanol + 60 ml of water |
| 9 | 6 g; Ar = (4-indolyl) | 6.35 g | 60 ml of ethanol + 20 ml of water |
| 10 | 10 g; Ar = (2-methyl-4-indolyl) | 10 g | 100 ml of ethanol + 30 ml of water |
| 11 | 9.15 g; Ar = (carbazolyl) | 4.5 g | 90 ml of ethanol + 18 ml of H₂O |

EXAMPLE 12

3-{3-[2-methyl-indolyl-(4)-oxy]-2-hydroxy-propylamino}-butyl guanidine

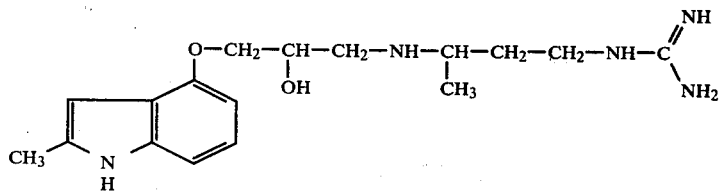

After filtration, the hydrogenation solution obtained as described below, which contains 3-{3-[2-methyl-indolyl-(4)-oxy]-2-hydroxypropylamino}-butylamine is reacted with S-methyl isothiourea sulphate (3.1 g in 13 ml of water) by boiling for 10 hours. A pH value of 5 is maintained using dilute sulphuric acid, after which the mixture is left standing for 10 hours. The product is then filtered off under suction and recrystallized from water. The yield is 3.9 g, and the m.p. of the sulphate is 242°–244° C. (contains 1 mole of water).

Production of the starting amine:

34.4 g of 1-[2-methylindolyl-(4)-oxy]-2,3-epoxy propane are reacted with 31 g of 1-benzylamino-3-aminobutane (produced from 1,3-diaminobutane and benzyl chloride in the presence of potassium carbonate, followed by fractional distillation in vacuo, b.p. 0.1 mm: 95°–96° C.) in 250 ml of dioxane for 4 hours at boiling temperature. The reaction product is distilled in vacuo and the residue is dissolved in ethylacetate. The ethylacetate solution is extracted by repeated shaking with aqueous tartaric solution, the combined aqueous phases are alkalized with 20% sodium hydroxide solution and subsequently extracted by shaking five times with dichloromethane. After drying with sodium sulphate, the product is filtered and concentrated by evaporation in a rotary evaporator.

The residue is then dissolved in 75 ml of acetone, followed by the addition of a solution of maleic acid in acetone (11.5 g in 50 ml acetone). On the next day, the product is filtered under suction, washed with ethanol and dried.

13.5 g of the maleate thus obtained (m.p. 162°–164° C.) are taken up in water, the solution is alkalized using 10% sodium hydroxide and repeatedly extracted by shaking with ether containing a litter ethanol. After drying with sodium sulphate and distillation, the residual base is dissolved in ethanol.

Following the addition of 0.7 g of a 10% palladium carbon, the solution is hydrogenated at 60° C. The resulting 3-{3-[2-methylindolyl-(4)-oxyl]-2-hydroxypropylamino}-butylamine is directly further reacted without isolation.

EXAMPLES OF PHARMACEUTICAL PREPARATIONS

EXAMPLE 13

Injection Solution 5 mg of the compound of Example 5 was dissolved in 200 mg of propylene glycol and the solution filled up with water to a total volume of 2 ml. After filtration, the solution was filled into ampoules.

EXAMPLE 14

| Tablets | |
| --- | --- |
| Active matter of Example 5 | 50.0 mg |
| Lactose | 79.1 mg |
| Polyvinyl pyrrolidone | 5 mg |
| Cornstarch | 15.0 mg |
| Highly dispersed silica | 0.5 mg |
| Magnesium stearate | 0.4 mg |

The active material was mixed with the lactose and cornstarch and moistened with a solution of the polyvinyl pyrrolidone in water; the composition thoroughly worked, dried, sieved and after addition of the highly dispersed silica and magnesium stearate compressed into tablets.

The entire disclosure of British priority application No. 35819/78 filed Sept. 6, 1978 is hereby incorporated by reference.

What is claimed is:

1. A substituted aminoalkyl guanidine corresponding to the following formula:

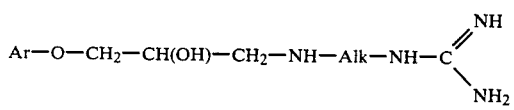

wherein Alk represents a $C_2$–$C_5$-alkylene group or such a group substituted by a hydroxy group and Ar represents indolyl and methyl indolyl or a pharmaceutically acceptable acid addition salt thereof.

2. A compound according to claim 1 wherein Ar is indolyl-(4)-or 2-methylindolyl-(4)-.

3. A compound according to claim 2 wherein Ar is 2-methyl indolyl-(4)-.

4. A compound according to claim 3 which is 3-{-[2-methyl-indolyl-(4)-oxy]-2-hydroxypropylamino}-butyl guanidine.

5. A compound according to claim 3 which is 3-{3-[2-methyl-indolyl-(4)-oxy]-2-hydroxypropylamino}-propyl guanidine.

6. A compound according to claim 2 which is 3-{3-[indolyl-(4)-oxy]-2-hydroxypropyl-amine}-propyl guanidine.

7. A medicament suitable for blocking of $\beta$-receptors of the adrenergic nerve system which comprises at least one substituted aminoalkyl guanidine as claimed in claim 1, together with at least one pharmacologically acceptable carrier.

8. A method of blocking the $\beta$-receptors of the adrenergic nerve system in a mammal comprising administering to the mammal an effective amount of a compound of claim 1 to block the $\beta$-receptors of the adrenergic nerve system.

9. A method according to claim 8 wherein the compound is administered orally.

10. A method according to claim 8 wherein the compound is administered intravenously.

11. A method according to claim 8 wherein Ar is 2-methyl indolyl-(4).

12. A method according to claim 11 wherein the compound is 3-{3-[2-methyl-indolyl-(4)-oxy]-2-hydroxypropylamino}-butyl guanidine.

13. A method according to claim 11 wherein the compound is 3-{3-[2-methyl-indolyl-(4)-oxy]-2-hydroxypropylamino}-propyl guanidine.

14. A method according to claim 11 wherein the compound is 3-{3-[indolyl-(4)-oxy]-2-hydroxypropylamino}-propyl guanidine.

* * * * *